United States Patent
Namba et al.

(10) Patent No.: US 7,208,643 B2
(45) Date of Patent: Apr. 24, 2007

(54) PROCESS FOR PRODUCING FATTY ALCOHOL

(75) Inventors: Masanori Namba, Wakayama (JP); Toru Sakamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 206 days.

(21) Appl. No.: 11/084,161

(22) Filed: Mar. 21, 2005

(65) Prior Publication Data

US 2005/0222469 A1    Oct. 6, 2005

(30) Foreign Application Priority Data

Apr. 2, 2004 (JP) .............................. 2004-109968

(51) Int. Cl.
   *C07C 29/149*    (2006.01)
(52) U.S. Cl. ................. 568/885; 568/876; 568/884
(58) Field of Classification Search ............... 568/885, 568/884, 876
   See application file for complete search history.

(56) References Cited

FOREIGN PATENT DOCUMENTS

| EP | 0 454 720 B1 | 11/1991 |
| EP | 1 042 260 | 10/2000 |
| WO | WO 90/08123 | 7/1990 |
| WO | WO 99/31035 | 6/1999 |

OTHER PUBLICATIONS

Theodor Voeste, et al., "Production of Fatty Alcohols from Fatty Acids", JAOCS, vol. 61, No. 2, Feb. 1984, pp. 350-352.
Patent Abstracts of Japan, JP 2001-131102, May 15, 2001.

*Primary Examiner*—Elvis O. Price
(74) *Attorney, Agent, or Firm*—Oblon, Spivak, McClelland, Maier & Neustadt, P.C.

(57) ABSTRACT

The invention relates to a process for producing a fatty alcohol, including hydrogenating a fatty acid ester to prepare a crude fatty alcohol product, and distilling and refining the resulting crude fatty alcohol to prepare a fatty alcohol, further including recovering a part or the whole of distillation residues obtained in the distillation step and removing an alkali component from the distillation residues, adding the treated distillation residues to hydrogenation step or to a starting fatty acid ester feed.

4 Claims, No Drawings

PROCESS FOR PRODUCING FATTY ALCOHOL

FIELD OF THE INVENTION

The present invention relates to a process for producing a fatty alcohol from a fatty acid ester as the starting material.

BACKGROUND OF THE INVENTION

The fatty alcohol is an important intermediate of various chemical products/household goods, demand therefor is significantly increasing in recent years, and there are extensive studies on processes producing the same at low cost while maintaining its qualities. Generally, the fatty alcohol is produced in the presence of a hydrogenation catalyst by catalytically reducing a starting material such as naturally occurring fat and oil, a fatty acid or a fatty acid ester, with hydrogen to form a crude fatty alcohol and then refining this product by distillation.

Generally, distillation residues generated in this distillation step have been disposed of so far, or as shown in "Production of Fatty Alcohols from Fatty Acids" by Theodor Voeste, JAOCS, Vol. 61, No. 2 (February 1984), pp. 350–352, a part of the residues have been recovered and mixed with a starting fatty acid and returned to the hydrogenation step.

In the fatty alcohol produced from a fatty acid ester through catalytic reduction, there remain a small amount of the unreacted fatty acid ester, and such fatty acid ester has a vapor pressure near to that of the fatty alcohol and is thus hardly separated therefrom. For the purpose of decomposition and removal of such unreacted ester, the addition of an alkali component at the time of distillation is known (EP-A 0454720). For the purpose of reducing impurities including carbonyl compounds such as aldehydes, the addition of an alkali component such as sodium borohydride or an aqueous solution of sodium hydroxide is known.

SUMMARY OF THE INVENTION

The present invention relates to a process for producing a fatty alcohol, including the steps of hydrogenating a fatty acid ester to prepare a crude fatty alcohol product (hereinafter referred to as hydrogenation step) and distilling and refining the resulting crude fatty alcohol product to prepare a fatty alcohol product (hereinafter referred to as distillation step), further including steps of recovering a part or the whole of distillation residues obtained in the distillation step and removing an alkali component from the recovered distillation residues, adding the treated distillation residues to hydrogenation step or a starting fatty acid ester feed.

DETAILED DESCRIPTION OF THE INVENTION

The addition of an alkali component such as in the prior art is effective for reducing impurities, but the added alkali component remains in distillation residues, and thus when the distillation residues are recovered and returned to the hydrogenation step, there is a problem of deterioration of a hydrogenation catalyst. In a suspended bed catalyst reactor, a part of the hydrogenation catalyst is replaced during operation by a new one, whereby the catalytic activity can be maintained, but when the hydrogenation reaction is continuously conducted in a fixed bed reactor having molded catalysts in a column, the catalyst cannot be exchanged during continuous production, thus making it impossible to recover and use distillation residues while the catalytic activity is maintained for a long time.

The present invention provides a process for producing a fatty alcohol by hydrogenating a fatty acid ester to form a crude fatty alcohol and then refining it by distillation, wherein the fatty alcohol is produced in high yield by recovering distillation residues without causing a reduction in the activity of a catalyst.

According to the process of the present invention, alcohol distillation residues can be used by recovery without causing a reduction in the activity of a catalyst for alcohol production, to produce a fatty alcohol in high yield.

[Hydrogenation Step]

The hydrogenation step of the present invention is a step of hydrogenating a fatty acid ester to give a crude fatty alcohol.

The starting fatty acid ester used in this step may be derived from either naturally occurring materials or synthetic materials. The fatty acid ester includes triglycerides, diglycerides and monoglycerides, as well as naturally occurring vegetable fats and oils and animal fats and oils based on mixtures of such glycerides. The vegetable fats and oils include, but are not limited to, rapeseed oil, soybean oil, coconut oil, palm oil, palm kernel oil, sunflower oil, sesame oil, corn oil, safflower oil and linseed oil, and the animal fats and oils include, but are not limited to, fish oil, tallow and lard. Waste fats and oils thereof and waste edible oils thereof can also be used as the starting material.

Other fatty acid esters include esters of fatty acids and alcohols constituting the fats and oils described above. The alcohols are not particularly limited. Given esters of higher alcohols, wax is formed. The industrial starting material is preferably esters of lower alcohols wherein the lower alcohols are preferably C1 to 10 fatty alcohols, more preferably about C1 to C5 lower alcohols such as methanol, ethanol and propanol. Among these, methanol is even more preferable from the viewpoint of cost and easiness in recovery.

Insofar as catalytic reduction reaction is feasible, a reactor for hydrogenation of fatty acid esters is not particularly limited, and may be a usually used reactor known in the art. Examples include a suspended bed reactor where the catalytic reduction reaction is carried out by fluidizing a catalyst with fluid and a fixed bed reactor where the catalytic reduction reaction is carried out by supplying fluid to a packed and fixed catalyst.

The hydrogenation catalyst used in this step may be a known catalyst used usually in hydrogenation, and is not particularly limited. Examples include catalysts based on copper, rhenium, cobalt and a noble metal etc.

The temperature of the hydrogenation reaction is preferably 100° C. or more, more preferably 150° C. or more, from the viewpoint of attaining sufficient reaction rates. At high temperatures, byproducts are formed more easily than formed alcohols, and thus the temperature is preferably 300° C. or less, more preferably 280° C. or less, still more preferably 250° C. or less. The reaction pressure is preferably a higher pressure from the viewpoint of shifting the reaction equilibrium toward the alcohol side, but in consideration of facility costs, the reaction pressure is preferably 1 to 30 MPa, more preferably 2 to 25 MPa, still more preferably 10 to 25 MPa.

From the starting fatty acid ester, the corresponding crude fatty alcohol is obtained in this step.

[Distillation Step]

The distillation step of the present invention is a step of distilling and refining the crude fatty alcohol obtained in the hydrogenation step to give a fatty alcohol.

In the distillation, an alkali component is preferably added to decompose the unreacted fatty acid ester in the crude fatty alcohol. The alkali component includes potassium hydroxide, sodium hydroxide, sodium borohydride etc. The amount of the alkali component added is preferably 1 to 1000 weight ppm, more preferably 10 to 100 weight ppm, relative to the crude fatty alcohol.

The distillation operation may be conducted in a column packed with irregular packing such as a metal plate or mesh for gas/liquid contact in the column or with irregular packing such as Raschig ring and Pall ring, a distilling column having trays such as porous trays or bubble cap trays arranged therein, Petlyuk system distillation column partially divided therein or a flash column not provided with a gas/liquid contact region in the column. This distillation operation can be carried out in continuous operation, batch operation or semi-batch operation. In this step, the supply of the crude fatty alcohol to the distilling column may be batch-wise or continuous, but is desirably continuous from the viewpoint of efficiency of production.

Although the distillation conditions can be suitably selected depending on the vapor pressure of the fatty alcohol to be produced, a temperature of 100 to 250° C. and a pressure of 0.1 to 30 kPa are preferably used.

By distillation, a refined fatty alcohol is obtained, while distillation residues are obtained from the bottom of the distilling column. The residues can be removed continuously or batch-wise.

[Recovery Step]

The recovery step in the present invention is a step of recovering a part or the whole of distillation residues obtained in the distillation step and removing the alkali component from the distillation residues followed by a hydrogenation step or adding the distillation residues to a starting fatty acid ester.

The method of removing the alkali component from the distillation residues includes a method that involves mixing water with the distillation residues and then separating them into an oil phase and an aqueous phase (hot water washing), a method that involves mixing water and an acid with the distillation residues and separating them into an oil phase and an aqueous phase (acid decomposition treatment) and a method that involves contacting the distillation residues with ion-exchange resin and then separating them into an oil phase and an aqueous phase (ion-exchange resin treatment method), among which the hot water washing and acid decomposition treatment are preferable.

In the hot water washing, the alkali component is removed by adding water or hot water to the residues and then stirring them. From the viewpoint of the efficiency of removal of the alkali component, the amount of water added to the residues is preferably 3 wt % or more, more preferably 5 wt % or more. From the viewpoint of reducing the amount of waste water, the amount of water added is preferably 100 wt % or less, more preferably 30 wt % or less, still more preferably 10 wt % or less.

From the viewpoint of handling and effect, the operation of washing with hot water is preferably carried out at a temperature of higher than the melting point of the residues. Depending on the composition of the residues, the operation temperature is preferably about 60 to 130° C., more preferably not higher than 100° C. that is the boiling point of water, still more preferably 95° C. or less from the viewpoint of suppressing the reduction in the amount of water caused by water vaporization or 70° C. or more, further more preferably 90° C. or more, from the viewpoint of inhibiting the foaming or emulsification caused by soap contained in the residues and improving separation into an oil phase and an aqueous phase. The residues and hot water or water may be heated respectively and then mixed with each other, or may be mixed with each other and then heated to the operation temperature. When hot water washing is conducted, a washing tank having a stirring mechanism is used preferably. The addition order of the residues and hot water or water, the addition method and the mixing method are not particularly limited, and a known means can be used.

The acid decomposition treatment is carried out by adding an acid to the residues or by mixing the residues with an aqueous acid solution. The acid decomposition treatment, similar to hot water washing, is conducted preferably in a washing tank having a stirring mechanism, and may be carried out simultaneously with hot water washing. The preferable operation temperature and the amount of hot water or water in using an aqueous acid solution are also the same as in hot water washing, and the operation is carried out preferably under stirring.

From the viewpoint of effect, the acid used is preferably an inorganic acid and is not particularly limited, and generally used acids such as hydrochloric acid, sulfuric acid, phosphoric acid and nitric acid may be used. From the viewpoint of corrosion, acids other than hydrochloric acid are preferable.

The acid decomposition treatment is conducted where the pH value of the oil/water mixture is used as a guide to the treatment. From the viewpoint of efficiency of removal of the alkali component, the pH value is preferably 7 or less, and a lower pH value is more effective, but from the viewpoint of inhibition of corrosion of facilities, the pH value is preferably 3 to 7 and more preferably adjusted to 4 to 6. The pH value is a value determined by measuring the pH of an aqueous phase at 25° C. with composite electrodes and a pH meter. The acid decomposition treatment is easy and effective without necessity for preparation and regeneration of resin, as compared with ion-exchange resin treatment.

The ion-exchange resin treatment can be carried out in a batch process or by a method of passing a fluid of residues through a column packed with cation-exchange resin of acid form, and may be combined with hot water washing. As the resin, any resin such as styrene resin, methacrylic resin and acrylic resin may be used, and the operation temperature is generally 120° C. or less, preferably 100° C. or less, depending on the working temperature of the resin.

By ion-exchange resin treatment and acid decomposition treatment, soap and wax in the residues are converted into fatty acids and alcohols, thus improving separation into an oil phase and an aqueous phase. Further, the soap and wax are converted without accumulation in the system into alcohols, thus improving the alcohol yield.

Treatments such as hot water treatment, acid decomposition treatment and ion exchange resin treatment can be performed more efficiently by combining the treatments with one another, or by conducting the treatment stepwise or repeatedly.

Removal of the alkali component by separation into an oil phase and an aqueous phase can be carried out by a known method exemplified by a gravity floating method utilizing a difference in gravity, a centrifugation method or a membrane separation method to give residues from which the alkali component was removed.

The distillation residues from which the alkali component was removed are retuned to the hydrogenation step or added to the starting fatty acid ester. The amount of the distillation residues added to the starting fatty acid ester is related to the total content of the alkali component after mixed, and to the alkali resistance of the hydrogenation catalyst used. That is, a larger amount of residues can be added as the content of the alkali component in the starting fatty acid ester is decreased or as the alkali resistance of the hydrogenation catalyst is increased. In the opposite case, it is important to remove the alkali component sufficiently from the distillation residues.

The distillation residues are added generally such that the total content of the alkali component becomes an amount of 60 ppm (by weight; hereinafter, ppm refers to ppm by weight) or less, preferably 30 ppm or less, more preferably 10 ppm or less, still more preferably 5 ppm or less, depending on the catalyst used. The content of the alkali component is a value determined by an atomic absorption spectrometer.

EXAMPLES

The present invention is described by reference to the Examples below. The Examples are described for mere illustrative purposes and not intended to limit the scope of the present invention.

Example 1

<Hydrogenation and Distillation>

Palm kernel oil-derived fatty methyl ester (saponification value 240 mg KOH/g determined by "Standard Fat and Oil Analysis Test Method" edited by JAPAN Oil Chemists' Society) was used as the starting material, and 200 g of this starting ester was subjected to hydrogenation reaction for 3 hours under the conditions of 285° C. and 24.5 MPa by circulating 5 L/min hydrogen therethrough in the presence of 3 g Cu—Cr hydrogenation catalyst (KSC-1 manufactured by Nikki Chemical Co., Ltd.) to give a crude fatty alcohol. Potassium hydroxide was added in an amount of 50 ppm (in terms of potassium) to the crude fatty alcohol, which was then subjected to distillation by charging it into a continuous distillation apparatus and heating it to a temperature of 232° C. in the top of a column at a vacuum degree of 1.6 kPa. The alkali component in the distillation residues, as determined by an atomic absorption spectrometer (Z-6100 manufactured by Shimadzu Corp)., was 1020 ppm.

<Removal of the Alkali Component>

The resulting distillation residues were charged into a stirring mixing apparatus, and hot water at 80° C. was added thereto in an amount of 90 wt % relative to the residues, which were then regulated to a temperature of 90° C. and stirred for 30 minutes. Then, the residues were adjusted to pH 2.4 with 20% aqueous sulfuric acid, and then stirred at 90° C. for 30 minutes. The residues were left at a kept temperature of 90° C. in a separatory funnel for 1 hour to separate them into an oil phase and an aqueous phase, to give distillation residues from which the alkali component had been removed. The alkali component in the distillation residues after subjection to removal of the alkali component was 2.5 ppm, indicating that 99.8% of the alkali component had been removed.

<Hydrogenation Reaction of the Recovered Residues>

20 g of the distillation residues from which the alkali component had been removed were added to 200 g palm kernel oil-derived fatty methyl ester (saponification value 240 mg KOH/g determined by "Standard Fat and Oil Analysis Test Method" edited by JAPAN Oil Chemists' Society) and charged into a 500-mL autoclave. The total content of the alkali component in the starting fatty acid ester was 3.9 ppm. The mixture was subjected to hydrogenation reaction for 3 hours under the conditions of 285° C. and 24.5 MPa by circulating 5 L/min hydrogen therethrough in the presence of 3 g Cu—Cr hydrogenation catalyst (KSC-1 manufactured by Nikki Chemical Co., Ltd.).

1.5 hours after the reaction was initiated, the saponification value (SV) was 7.5 mg KOH/g. When the SV became 5 mg KOH/g as a result of progress of the reaction, the amount of hydrocarbon (HC) was 0.34% (by gas chromatography).

Reference Example 1

In the hydrogenation reaction of the recovered residues in Example 1, the fatty methyl ester used in Example 1 was charged into a 500-mL autoclave but the distillation residues from which the alkali component had been removed were not charged into the autoclave, and the hydrogenation reaction was conducted under the same conditions as in Example 1.

1.5 hours after the reaction was initiated, the saponification value (SV) was 5.7 mg KOH/g. When the SV became 5 mg KOH/g as a result of progress of the reaction, the amount of hydrocarbon (HC) was 0.35%.

Comparative Example 1

In Example 1, 20 g distillation residues obtained without conducting removal of the alkali component were added to 200 g fatty methyl ester used in Example 1 and charged into a 500-mL autoclave. The total content of the alkali component in the starting fatty acid ester was 96 ppm. Thereafter, the mixture was subjected to hydrogenation reaction under the same conditions as in Example 1.

1.5 hours after the reaction was initiated, the saponification value (SV) was 111 mg KOH/g. When the SV became 5 mg KOH/g as a result of progress of the reaction, the amount of hydrocarbon (HC) was 0.48%.

The results in Example 1, Reference Example 1 and Comparative Example 1 are shown in Table 1. When the starting methyl ester was added to the distillation residues not subjected to alkali removal treatment (Comparative Example 1), the saponification value was hardly lowered in the reaction, indicating a reduction in the catalytic activity. On the other hand, when the distillation residues subjected to alkali removal treatment with hot water and an acid were added (Example 1), a similar reduction in saponification value to that in the reaction without adding the distillation residues (Reference Example 1) was observed, indicating that a reduction in the catalytic activity can be prevented.

TABLE 1

| | SV, 1.5 hours after reaction was initiated (mg-KOH/g) | Amount of HC at the time of SV = 5 (percentage of area in gas chromatography) |
| --- | --- | --- |
| Example 1 | 7.5 | 0.34 |
| Reference example 1 | 5.7 | 0.35 |
| Comparative example 1 | 111.0 | 0.48 |

Example 2

<Hydrogenation and Distillation>

The palm kernel oil-derived fatty methyl ester used in Example 1 was subjected to hydrogenation reaction by passing it at an LHSV of 0.75 (1/H) through a reaction column having an inner diameter of 25 mmφ and a catalyst layer length of 2 m packed with 500 cc of a Cu—Cr hydrogenation catalyst (N202D manufactured by Nikki Chemical Co., Ltd.), to give a crude fatty alcohol. The reaction conditions were temperature, 220° C.; pressure, 20 MPa; and hydrogen/methyl ester (molar ratio)=100. Potassium hydroxide was added in an amount of 50 ppm (in terms of potassium) to the crude fatty alcohol, charged into a continuous distillation apparatus and heated to 232° C. at the top of the column at a vacuum degree of 1.6 kPa, and the distillation operation was conducted. The alkali component in the distillation residues was 1138 ppm.

<Removal of the Alkali Component>

The resulting distillation residues were charged into a stirring mixing apparatus, and hot water at 80° C. was added thereto in an amount of 5 wt % relative to the residues, which were then regulated to a temperature of 90° C. and stirred for 30 minutes. Then, the residues were adjusted to pH 5.0 with 20% aqueous sulfuric acid, and then stirred at 90° C. for 30 minutes. The residues were left at a kept temperature of 90° C. in a separatory funnel for 1 hour to separate them into an oil phase and an aqueous phase, to give distillation residues from which the alkali component had been removed. The alkali component in the distillation residues after subjection to removal of the alkali component was 148 ppm, indicating that 87% of the alkali component had been removed.

<Hydrogenation Reaction of the Recovered Residues>

The distillation residues from which the alkali component had been removed were added in an amount of 1.3% to the same starting fatty methyl ester as in Example 1 to prepare recovered distillation residues/starting methyl ester. The total content of the alkali component in the recovered distillation residues/starting methyl ester was 1 ppm. The recovered distillation residues/starting methyl ester was subjected to hydrogenation reaction by passing it at an LHSV of 0.75 (1/H) through a reaction column having an inner diameter of 25 mmφ and a catalyst layer length of 2 m packed with 500 cc Cu—Cr hydrogenation catalyst (N202D manufactured by Nikki Chemical Co., Ltd.). The hydrogenation reaction conditions were temperature, 220° C.; pressure, 20 MPa; and hydrogen/methyl ester (molar ratio)=100.

After the reaction was finished, the saponification value (SV) was 11.7 mg KOH/g, and the amount of hydrocarbon (HC) was 0.01% (by gas chromatography).

Reference Example 2

The fatty methyl ester was subjected to hydrogenation reaction under the same conditions as in Example 2 except that the distillation residues from which the alkali component had been removed were not added in the hydrogenation reaction of the recovered residues in Example 2.

After the reaction was finished, the saponification value (SV) was 11.2 mg KOH/g, and the amount of hydrocarbon (HC) was 0.02%.

The results in Examples 2 and Reference Example 2 are shown in Table 2. When the distillation residues from which the alkali component had been removed with hot water and an acid were added (Example 2), a similar reduction in saponification value to that in the reaction without adding the distillation resides (Reference Example 2) was observed, indicating that a reduction in the catalytic activity can be prevented.

TABLE 2

| | SV, after reaction was finished (mg-KOH/g) | Amount of HC after reaction was finished (percentage of area in gas chromatography) |
|---|---|---|
| Example 2 | 11.7 | 0.01 |
| Reference example 2 | 11.2 | 0.02 |

Examples 3 to 8

The results of removal of the alkali component, wherein various distillation residues having the alkali concentrations shown in Table 3 were subjected to the various hot water addition and acid addition treatments shown in Table 3, are shown in Table 3. It was revealed that 69.0% of the alkali component is removed by only hot water treatment (Example 3), and by combination thereof with acid treatment, the alkali component is removed more efficiently.

TABLE 3

| | Condition for removal of alkali component | | | | Alkali concentration | | |
|---|---|---|---|---|---|---|---|
| | Amount of water added (wt-% relative to residues) | Stirring temperature after water addition (° C.) | pH after addition of acid | Stirring temperature after acid addition (° C.) | Distillation residues (ppm) | After alkali removal (ppm) | Degree of alkali removal (%) |
| Example 3 | 30 | 90 | *1 | — | 12300 | 3800 | 69.0 |
| Example 4 | 30 | 70 | 7.0 | 90 | 12300 | 139 | 98.9 |
| Example 5 | 10 | 70 | 7.0 | 90 | 12300 | 400 | 96.7 |
| Example 6 | 5 | 70 | 7.2 | 90 | 1138 | 122 | 89.3 |
| Example 7 | 10 | 90 | 7.0 | 90 | 1138 | 43 | 96.3 |
| Example 8 | 10 | 90 | 5.4 | 90 | 5800 | 113 | 98.1 |

Note)
*1: The pH after water addition in Example 3 was 9.8.

The invention claimed is:

1. A process for producing a fatty alcohol, comprising the steps of hydrogenating a fatty acid ester to prepare a crude fatty alcohol product (hereinafter referred to as hydrogenation step) and distilling and refining the resulting crude fatty alcohol product to prepare a fatty alcohol product (hereinafter referred to as distillation step), further comprising steps of recovering a part or the whole of distillation residues obtained in the distillation step and removing an alkali component from the recovered distillation residues, adding the treated distillation residues to hydrogenation step or a starting fatty acid ester feed.

2. The process according to claim 1, wherein the hydrogenation is carried out in a fixed bed.

3. The process according to claim 1 or 2, wherein the removal of the alkali component is carried out by mixing the distillation residues with water and then separating them into an oil phase and an aqueous phase.

4. The process according to claim 1 or 2, wherein the removal of the alkali component is carried out by mixing the distillation residues with an acid and water and then separating them into an oil phase and an aqueous phase.

* * * * *